(12) United States Patent
Singer

(10) Patent No.: US 6,193,751 B1
(45) Date of Patent: Feb. 27, 2001

(54) TRACHEOSTOMA VALVE WITH SPRING-LOADED PISTON

(76) Inventor: Mark I. Singer, 5 Gilmartin Ct., Tiburon, CA (US) 94920

( * ) Notice: Subject to any disclaimer, the term of this patent is extended or adjusted under 35 U.S.C. 154(b) by 0 days.

(21) Appl. No.: 09/184,497

(22) Filed: Nov. 2, 1998

(51) Int. Cl.$^7$ .................................................. A61F 2/20
(52) U.S. Cl. ........................................ 623/9; 128/207.16
(58) Field of Search ........................... 623/9; 128/207.14, 128/207.15, 207.16

(56) References Cited

U.S. PATENT DOCUMENTS

| | | |
|---|---|---|
| 4,325,366 | 4/1982 | Tabor . |
| 4,538,607 * | 9/1985 | Saul .......................................... 623/9 |
| 4,582,058 | 4/1986 | Depel et al. . |
| 5,059,208 | 10/1991 | Coe et al. . |
| 5,738,095 * | 4/1998 | Persson .................................... 623/9 |
| 5,937,857 * | 8/1999 | Caterini et al. .................. 128/207.16 |
| 5,950,620 * | 9/1999 | Stricklin .......................... 128/207.16 |

* cited by examiner

Primary Examiner—Bruce Snow
(74) Attorney, Agent, or Firm—Jack Lo

(57) ABSTRACT

A tracheostoma valve includes a tubular housing with an inner aperture at an inner end, and a smaller outer aperture at an outer end. The inner end of the valve is for being attached to a stoma of a patient. A shaft is positioned axially within the housing, and a rigid piston is slidable along the shaft. The piston has a smaller diameter than the interior diameter of the tubular housing, so that air can flow around it. The piston is movable between an open position intermediate of the inner and outer apertures, and a closed position against the outer aperture. The piston is biased by a spring to the open position when the air pressure is relatively low, such as during relaxed respiration, so that air may flow through the valve in either direction. At a high enough expiratory air pressure, such as that used for producing speech, the spring is collapsed and the piston is moved against the outer aperture. Expiratory air is thus diverted from the trachea into the pharynx through a conventional voice prosthesis positioned there between for producing speech.

8 Claims, 3 Drawing Sheets

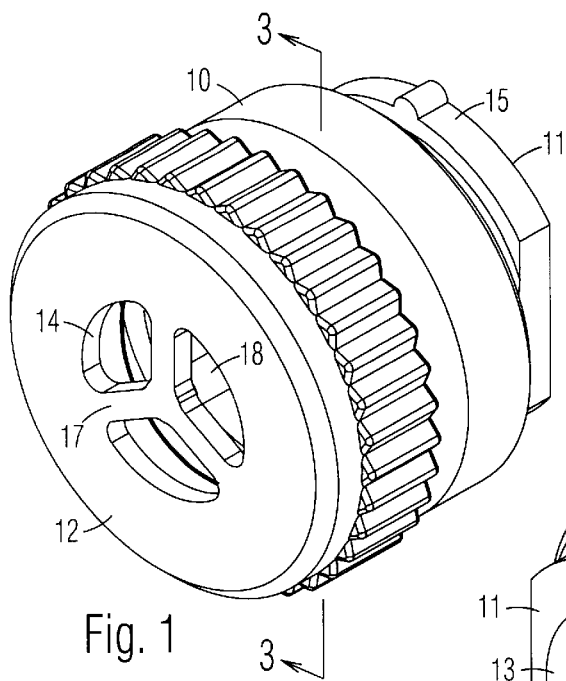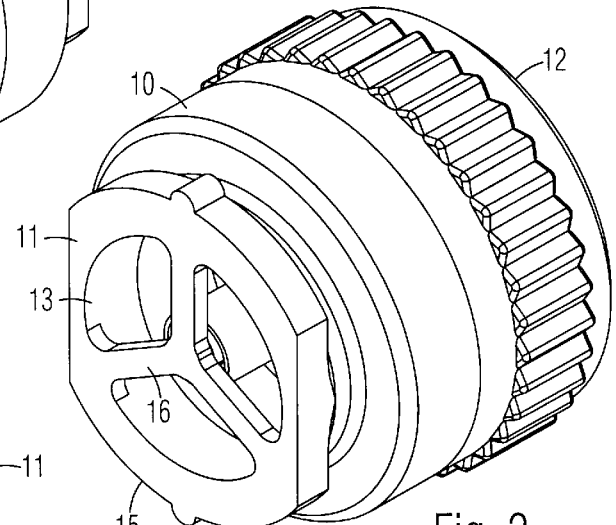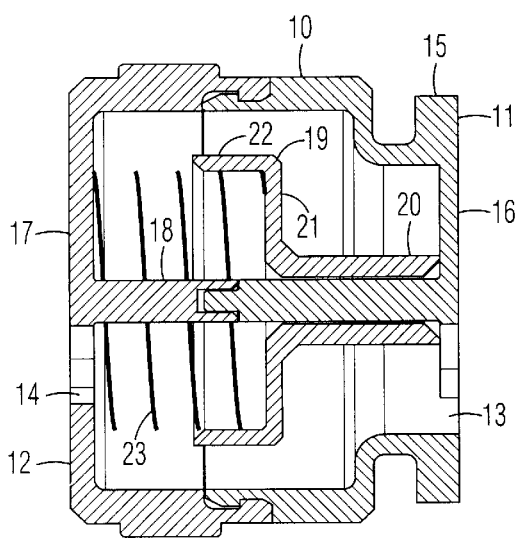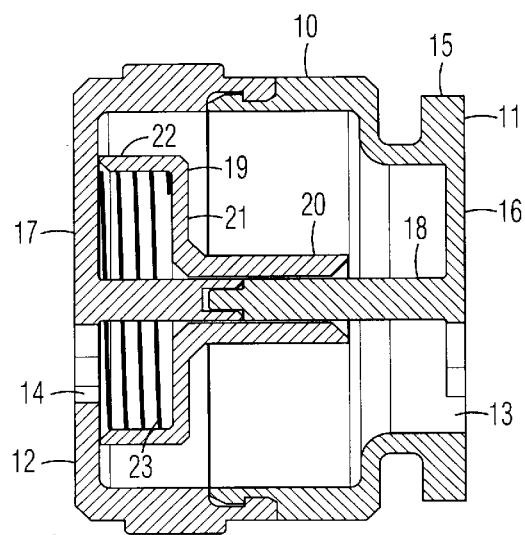

TRACHEOSTOMA VALVE WITH SPRING-LOADED PISTON

BACKGROUND OF THE INVENTION

1. Field of the Invention

This invention relates generally to tracheostoma valves.

2. Prior Art

In a human, a tube called the pharynx extends from the mouth down to the collarbone. A tube called the esophagus is connected between the pharynx and the stomach. A cartilaginous structure called the trachea is connected to the junction between the pharynx and the esophagus. A tube called the trachea is connected between the larynx and the lungs. Speech is produced by passing expiratory air from the trachea through the larynx and vibrating the vocal cords. The expiratory air is passed through the pharynx and out the mouth.

Sometimes the removal of the larynx, including the vocal cords, is necessitated by disease or injury. The trachea is diverted to exit the body at the base of the neck through a stoma (opening) to enable breathing. A tracheostoma valve is sometimes installed at the stoma for enabling bi-directional airflow during normal breathing. The valve is automatically closed under higher exhale pressures to redirect air from the trachea into the pharynx through a speech prosthesis extending there between. Speech is created by vibrating the air with muscles in the pharynx. The valve is sometimes installed at the end of a plastic tube inserted into the outer end of the trachea, and sometimes installed in a ring glued around the stoma.

U.S. Pat. Nos. 5,059,208 to Coe et al.; 4,582,058 to Depel et al.; and 4,325,366 to Tabor show tracheostoma valves. They are each comprised of a tubular housing with a flexible flapper membrane positioned close to a valve seat. The flapper membrane is normally spaced from the seat to allow bi-directional air flow during relaxed respiration. The flapper membrane is closed against the seat under higher exhale pressures to redirect air into the pharynx for speech production. However, the flapper membrane tends to flex too far away from the seat under high enough inhale pressure, such as that encountered during coughing, so that it would snap back onto the seat and make an embarrassing popping sound. The flapper membrane can only properly flex a small amount, so that it must be very close to the seat. The small gap between the flapper membrane and the seat tends to become clogged with body secretions, which makes the valve inoperative. Secretions also tend to foul the surface of the flapper membrane and prevent it from flexing properly.

OBJECTS OF THE INVENTION

Accordingly, objects of the present tracheostoma valve are:

- to remain open at a low air pressure for enabling bi-directional airflow during relaxed respiration;
- to close at a higher expiratory air pressure to redirect airflow into the pharynx for producing speech;
- to close with reduced effort by the patient; and
- to operate reliably in the presence of body secretions.

Further objects of the present invention will become apparent from a consideration of the drawings and ensuing description.

BRIEF SUMMARY OF THE INVENTION

A tracheostoma valve includes a tubular housing with an inner aperture at an inner end, and a smaller outer aperture at an outer end. The inner end of the valve is for being attached to a stoma of a patient. A shaft is positioned axially within the housing, and a rigid piston is slidable along the shaft. The piston has a smaller diameter than the interior diameter of the tubular housing, so that air can flow around it. The piston is movable between an open position intermediate of the inner and outer apertures, and a closed position against the outer aperture. The piston is biased by a spring to the open position when the air pressure is relatively low, such as during relaxed respiration, so that air may flow through the valve in either direction. At a high enough expiratory air pressure, such as that used for producing speech, the spring is collapsed and the piston is moved against the outer aperture. Expiratory air is thus diverted from the trachea into the pharynx through a conventional voice prosthesis positioned there between for producing speech.

BRIEF DESCRIPTION OF THE SEVERAL VIEWS OF THE DRAWING

FIG. 1 is a front perspective view of the present tracheostoma valve.

FIG. 2 is a rear perspective view of the valve.

FIG. 3 is a side sectional view of the valve in an open position, taken along line 3—3 in FIG. 1.

FIG. 4 is a side sectional view of the valve in a closed position.

DRAWING REFERENCE NUMERALS

Figure 5:
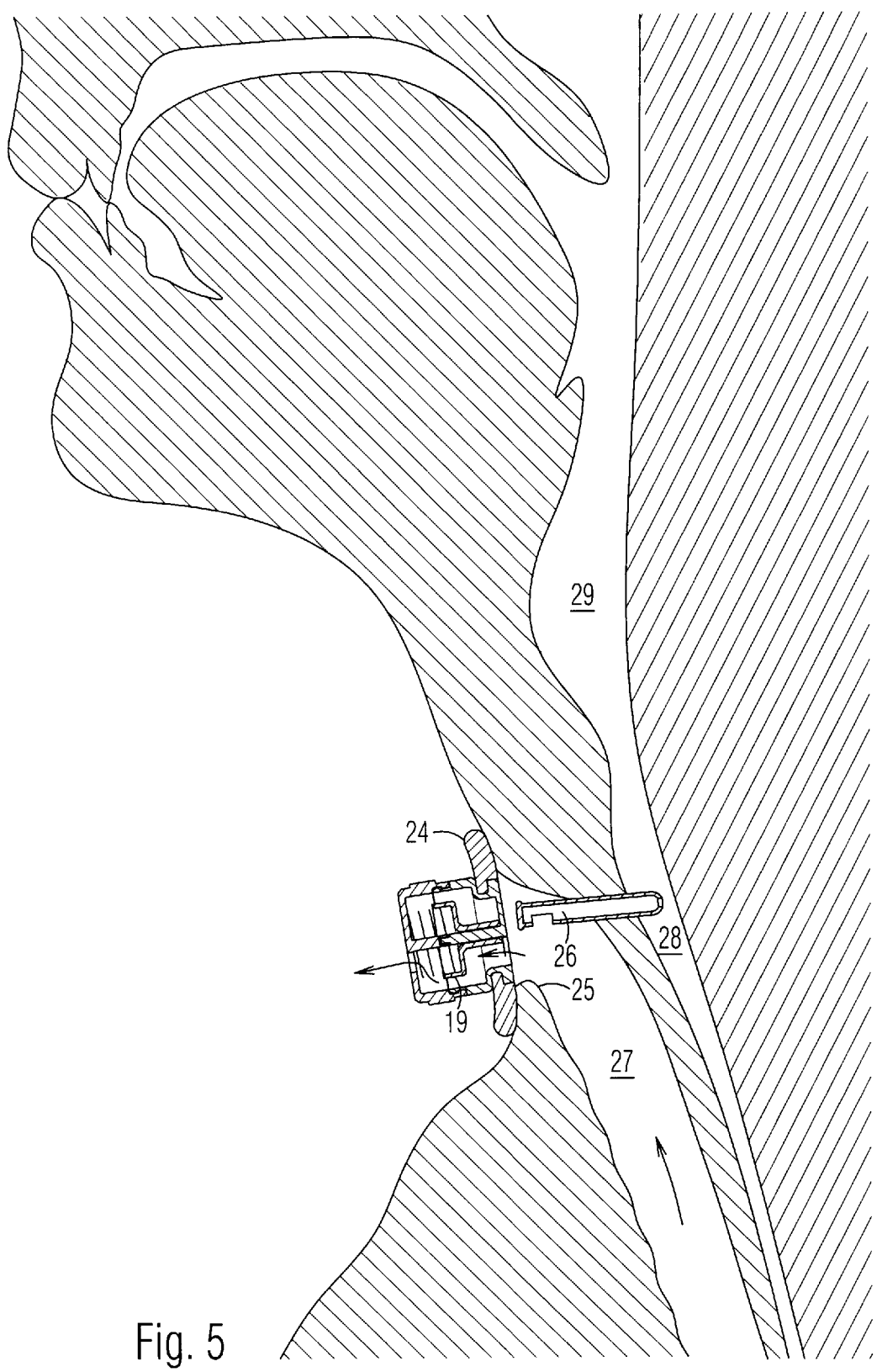
FIG. 5 is a side sectional view of the valve installed on a patient, and in an open position.

10. Housing
11. Inner End
12. Outer End
13. Inner Aperture
14. Outer Aperture
15. Mounting Flange
16. Spokes
17. Spokes
18. Shaft
19. Piston
20. Sleeve
21. Disc
22. Ring
23. Spring
24. Mounting Ring
25. Stoma
26. Speech Prosthesis
27. Trachea
28. Esophagus
29. Pharynx

DETAILED DESCRIPTION OF THE INVENTION

FIGS. 1–2:

A preferred embodiment of the present tracheostoma valve is shown in a front perspective view in FIG. 1, and a rear perspective view in FIG. 2. It is comprised of a tubular housing 10 with an inner end 11, and an outer end 12. An inner aperture 13 is arranged at inner end 11, and a smaller outer aperture 14 is arranged at outer end 12. A mounting flange 15 is positioned at inner end 11 for connecting to a conventional mounting tube (not shown) inserted into a trachea through a stoma, or a mounting ring (not shown)

glued around the stoma. Spokes 16 are attached within inner aperture 11, and spokes 17 are attached within outer aperture 14. A shaft 18 positioned axially within housing 10 is connected between the centers of spokes 16 and 17.

FIGS. 3–4:

The tracheostoma valve is shown in side sectional views in FIGS. 3 and 4. A piston 19 coaxial with shaft 18 is smoothly slidable thereon. Piston 19 is preferably comprised of a sleeve 20 sized to fit closely but movably around shaft 18, a disc 21 attached to sleeve 20 and coaxial therewith, and a ring 22 extending forwardly from the rim of disc 21. Piston 19 is larger in diameter than outer aperture 14. In FIG. 3, piston 19 is biased to an open position intermediate of inner aperture 13 and outer aperture 14 by a compression spring 23 disposed between piston 19 and outer end 12 of housing 10. Piston 19 is substantially smaller in diameter than the interior diameter of housing 10, so that air may freely flow around it. Spring 23 is kept in coaxial alignment with piston 19 by ring 22.

Piston 19 is kept in the open position by spring 23 when the airflow is at a relatively low pressure, such as during relaxed respiration, so that air may flow through the valve in either direction. At a high enough expiratory or exhale air pressure, spring 23 is collapsed and piston 19 is moved into abutting engagement with the rim of outer aperture 14 and thus close the valve, as shown in FIG. 4. The force of spring 23 may be varied to enable valve closure at a variety of air pressures suitable for different patients.

When expiratory air is flowing out through outer aperture 14, the air pressure is greater at the inner side of piston 19 than at the outer side. Further, a venturi-effect is created at outer aperture 14 due to its smaller size relative to inner aperture 13, i.e., the airflow velocity is increased and the air pressured is decreased at outer aperture 14 relative to inner aperture 13. An even greater pressure differential is thus created between the inner and outer sides of piston 19, so that piston 19 is moved to the closed position with less effort by a patient.

FIGS. 5–6:

The tracheostoma valve is shown in FIG. 5 installed in a conventional mounting ring 24 glued around a stoma 25 of a patient. A conventional speech prosthesis 26 is installed between a trachea 27 and the junction between an esophagus 28 and a pharynx 29. During relaxed respiration, piston 19 is kept in the open position, so that air is allowed to pass through the valve in either direction. Air is not passed through speech prosthesis 26 when the valve is open.

Figure 6:
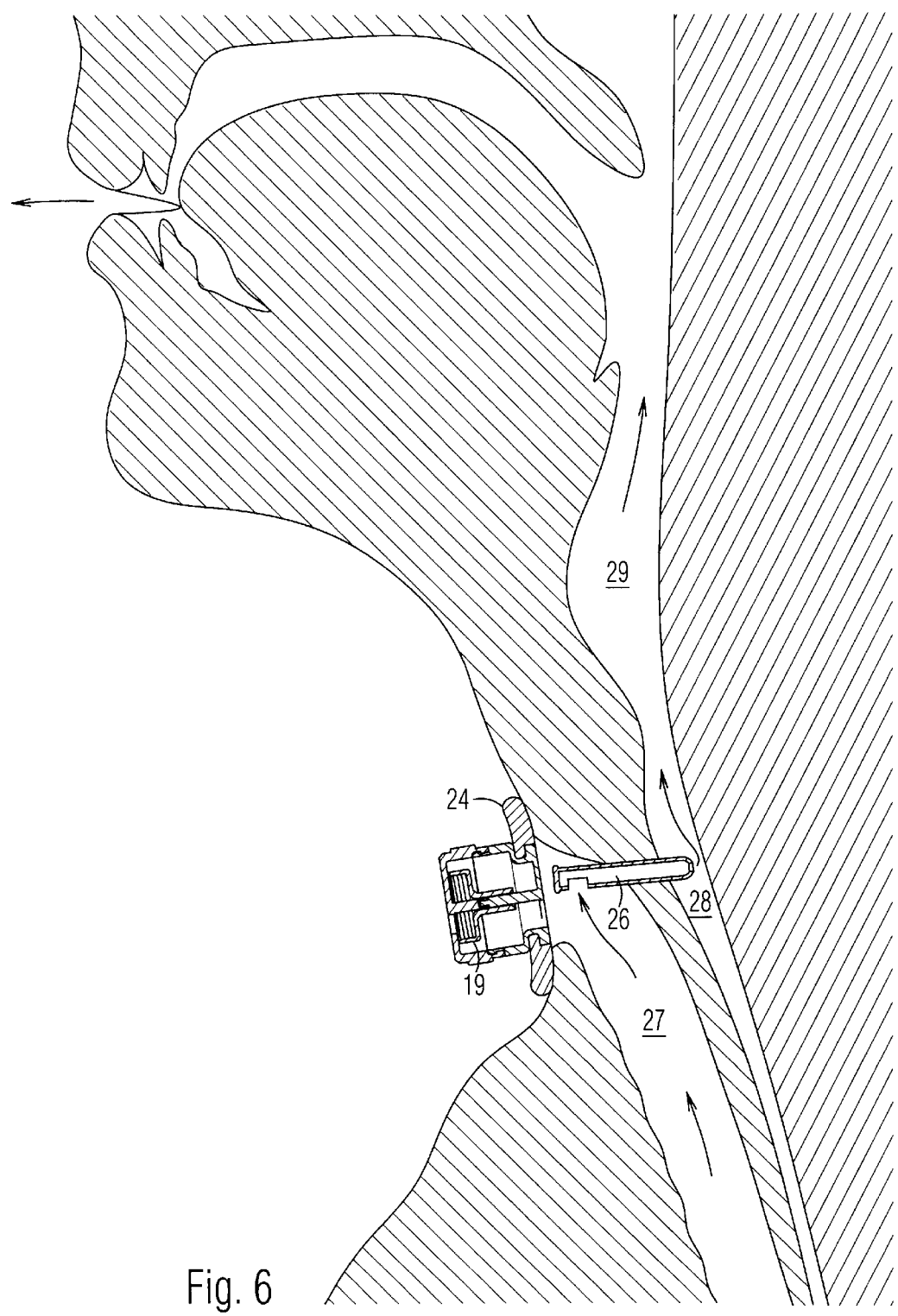
FIG. 6 is a side sectional view of the valve installed on a patient, and in a closed position.

When expiratory airflow is at a high enough pressure, such as during speech production, piston 19 is moved to the closed position shown in FIG. 6. Airflow from trachea 27 is thus redirected entirely through speech prosthesis 26 for producing speech in pharynx 29. Piston 19 is returned to the open position by inhaling. The gap between piston 19 and aperture 14 is large enough to avoid being clogged by body secretions. Also, unlike prior art flapper membrane valves, the movement of rigid piston 19 is not affected by body secretions.

SUMMARY AND SCOPE

Accordingly, an improved tracheostoma valve is provided. It is kept open at a low air pressure for enabling bi-directional airflow during relaxed respiration. It is closed at a higher expiratory air pressure to redirect airflow into the pharynx for producing speech. It is closed with reduced effort by the patient. It is also arranged to operate reliably in the presence of body secretions.

Although the above description is specific, it should not be considered as a limitation on the scope of the invention, but only as an example of the preferred embodiment. Many variations are possible within the teachings of the invention. For example, the size of the inner and outer apertures may be varied for allowing different rates of airflow. Instead of a compression spring positioned between the outer end of the housing and the outer side of the piston, an extension spring may be connected between the inner end of the housing and the inner side of the piston. Other types of springs may be provided. The piston may be of other shapes. The valve may be attached to the patient in other ways and locations. The valve may be used with any type of speech prosthesis. Therefore, the scope of the invention should be determined by the appended claims and their legal equivalents, not by the examples given.

I claim:

1. A valve for assisting breathing and vocalization, comprising:
    a tubular housing with an inner end for being attached to a respiratory system of a patient, said housing having an outer end;
    an inner aperture arranged at said inner end of said housing;
    an outer aperture arranged at said outer end of said housing; and
    a piston positioned within said housing, said piston comprising a disc and a ring, said ring extending forwardly from said disc toward said outer end, said piston being movable with a linear sliding motion between an open position away from said inner aperture and said outer aperture, and a closed position in engagement against said outer end, said piston enabling airflow between said inner aperture and said outer aperture when in said open position so as to enable breathing, said piston blocking airflow through said outer aperture when in said closed position so as to enable vocalization.

2. The valve of claim 1, wherein said piston further includes a sleeve movably positioned around a shaft extending between said inner aperture and said outer aperture, said disc being attached to said sleeve in coaxial alignment.

3. The valve of claim 1, wherein said piston is substantially smaller than an inner diameter of said housing for enabling airflow around said piston.

4. The valve of claim 1, wherein said outer aperture is substantially smaller than said inner aperture for providing a venturi effect at said outer aperture for helping draw said piston toward said outer end.

5. The valve of claim 1, further including a spring biasing said piston to said open position.

6. The valve of claim 1, further including a mounting flange arranged at said inner end for mounting to said patient.

7. The valve of claim 1, further including a shaft extending between said inner aperture and said outer aperture, said piston being positioned around said shaft and slidable along said shaft.

8. The valve of claim 1, further including a shaft extending between said inner aperture and said outer aperture, said piston being positioned around said shaft and slidable along said shaft, and also including an outer set of spokes arranged at said outer aperture attached to one end of said shaft, and an inner set of spokes arranged at said inner aperture attached to another end of said shaft.

\* \* \* \* \*